United States Patent
Yano et al.

(10) Patent No.: US 6,693,175 B2
(45) Date of Patent: Feb. 17, 2004

(54) METHOD FOR DIAGNOSING BONE DYSBOLISM

(75) Inventors: Kazuki Yano, Tochigi (JP); Fumie Kobayashi, Tochigi (JP); Masaaki Goto, Tochigi (JP); Naohiro Washida, Tochigi (JP); Eisuke Tsuda, Tochigi (JP); Kanji Higashio, Saitama (JP); Yoshiji Yamada, Aichi (JP)

(73) Assignee: Sankyo Co., Ltd., Tokyo (JP)

( * ) Notice: Subject to any disclaimer, the term of this patent is extended or adjusted under 35 U.S.C. 154(b) by 30 days.

(21) Appl. No.: 09/308,800

(22) PCT Filed: Jul. 31, 1998

(86) PCT No.: PCT/JP98/03421

§ 371 (c)(1),
(2), (4) Date: May 24, 1999

(87) PCT Pub. No.: WO99/15691

PCT Pub. Date: Apr. 1, 1999

(65) Prior Publication Data

US 2002/0004207 A1 Jan. 10, 2002

(30) Foreign Application Priority Data

Sep. 24, 1997 (JP) ............................................. 9/276475

(51) Int. Cl.$^7$ .......................... C07K 16/00; C12P 21/08
(52) U.S. Cl. ..................... 530/388.1; 435/7.1; 435/7.2; 435/7.71; 435/7.23; 435/7.92; 435/7.94; 435/69.7; 435/69.1; 435/181; 530/350; 530/388.24; 530/388.26; 530/388.15; 530/300; 530/387.3; 530/388.2; 530/388.55; 530/389.1; 530/387.1; 530/809; 514/12; 514/24; 424/133.1; 424/141.1; 424/172.1; 424/184.1; 800/14
(58) Field of Search .................... 514/24, 12, 2; 800/14; 435/69.7, 69.1, 181, 7.1, 7.2, 7.71, 7.92, 7.23, 709, 7.94; 530/809, 350, 388.1, 388.26, 388.15, 300, 387.3, 388.2, 388.85, 389.1, 387.1; 424/133.1, 152.1, 172.1, 184.1; 436/527

(56) References Cited

U.S. PATENT DOCUMENTS

| | | | |
|---|---|---|---|
| 4,179,337 A | 12/1979 | Davis et al. | 435/181 |
| 5,118,667 A | 6/1992 | Adams et al. | 514/12 |
| 5,366,859 A | * 11/1994 | Miyoshi et al. | 435/5 |
| 5,374,529 A | * 12/1994 | Caterson et al. | 435/7.1 |
| 5,393,739 A | 2/1995 | Bentz et al. | 514/12 |
| 5,427,954 A | * 6/1995 | Sandy et al. | 436/89 |
| 5,447,851 A | 9/1995 | Beutler et al. | 435/69.7 |
| 5,578,569 A | 11/1996 | Tam | 514/12 |
| 5,599,708 A | 2/1997 | Mundy et al. | 435/240.27 |
| 5,658,756 A | 8/1997 | Rodan et al. | 435/69.1 |
| 5,830,850 A | * 11/1998 | Gelb et al. | 514/2 |
| 5,843,678 A | 12/1998 | Boyle | 435/7.1 |
| 5,985,832 A | 11/1999 | Roodman et al. | 514/12 |
| 6,015,938 A | * 1/2000 | Boyle | 800/18 |
| 6,017,729 A | 1/2000 | Anderson et al. | 435/69.1 |
| 6,046,033 A | * 4/2000 | Goto | 435/69.1 |

FOREIGN PATENT DOCUMENTS

| | | | |
|---|---|---|---|
| EP | 0 514 130 A2 | 11/1992 | A61K/37/02 |
| EP | 0 727 211 A1 | 8/1996 | A61K/31/50 |
| EP | 784 093 | * 7/1997 | C12N/15/12 |
| EP | 816 380 | * 1/1998 | C07K/14/52 |
| NZ | 330400 | 5/1999 | |
| WO | 96/26217 | * 8/1996 | C07K/14/52 |
| WO | WO 96/28546 | 9/1996 | |
| WO | 97/00317 | 1/1997 | C12N/15/11 |
| WO | 97/00318 | 1/1997 | C12N/15/11 |
| WO | 97/23614 | * 7/1997 | C12N/15/12 |
| WO | 98/07840 | 2/1998 | C12N/15/00 |

OTHER PUBLICATIONS

Tsuda, E et al, Biochem. Biophys Res Commun, May 8, 1997, vol. 234(1), pp. 137–142, Isolation of a novel cytokine from human fibroblasests that specifically inhibits osteoclastogenesis.*

Simonet et al., "Osteoprotegerin: a novel secreted protein involved in the regulation of bone density," CELL, vol. 89, Apr. 18, 1997, pp. 309–319.

Reddi, "Bone morphogenesis and modeling: soluble signals sculpt osteosomes in the solid state," CELL, vol. 89, Apr. 18, 1997, pp. 159–161.

Tsuda et al., "Isolation of a novel cytokine from human fibroblasts that specifically inhibits osteoclastogenesis," Biochem. and Biophys. Research Commun., vol. 234, May 8, 1997, pp. 137–142.

Chambers et al., "Generation of osteoclast–inductive and osteoclastogenic cell lines from the H–2btsA58 transgenic mouse," Proceed. of the National Acad. of Sciences of USA, vol. 90, Jun. 1993, pp. 5578–5582.

Smith et al., "The TNF superfamily of cellular and viral proteins: activation, costimulation, and death," CELL, vol. 76, Mar. 25, 1994, pp. 959–962.

(List continued on next page.)

Primary Examiner—Lynette R. F. Smith
Assistant Examiner—Ginny Allen Portner
(74) Attorney, Agent, or Firm—Arnold & Porter (57) ABSTRACT

A method of diagnosing metabolic bone diseases, especially osteoporosis and arthrosis characterized by determining the concentration of osteoclastgenesis inhibitory factor (OCIF) in humor.

Monoclonal antibodies recognizing equally both of monomer type and dimer type of OCIF. Monoclonal antibodies recognizing selectively dimer type of OCIF. And to provide an assay kit for determination of OCIF concentration comprising the aforementioned two antibodies recognizing different epitope of OCIF and having high affinity showing dissociation constant of less than $2 \times 10^{-7}$ M with antigen. It is useful for a method of diagnosing metabolic bone diseases, especially osteoporosis and arthrosis or for an assay reagent for research thereof.

72 Claims, 6 Drawing Sheets

OTHER PUBLICATIONS

Goodwin et al., "Molecular cloning and expression of the type 1 and type 2 receptors for tumor necrosis factor," Database EMROD, EMBL Databases, Accession No: M59378, Jun. 28, 1991.

Chenu et al., "Transforming growth factor β inhibits formation of osteoclast–like cells in long–term human marrow cells," Proceed. of the National Acad. of Sciences of USA, vol. 85, Aug. 1998, pp. 5683–5687.

Gowen et al., "Preferential Inhibition of Cytokine–Stimulated Bone Resorption by Recombinant Interferon Gamma," Journal of Bone and Mineral Research, vol. 1, No. 5, 1986, pp. 469–474.

Hattersley et al., "Human Macrophage Colony–Stimulating Factor Inhibits Bone Resorption by Osteoclasts Disaggregated From Rat Bone," Journal of Cellular Physiology, vol. 137, No. 1, Oct. 1998, pp. 199–203.

Takada et al., "A simple method to assess osteoclast–mediated bone resorption using unfractionated bone cells," Bone and Mineral, vol. 17, 1992, pp. 347–359.

Kasono et al., "Inhibitory effect of interleukin–4 on osteoclast–like cell formation in mouse bone marrow culture," Bone and Mineral, vol. 21, 1993, pp. 179–188.

Watanabe et al., "Interleukin–4 as a Potent Inhibitor of Bone Resorption," Biochem. and Biophys. Research Comm., vol. 172, No. 3, Nov. 1990, pp. 1035–1041.

Adams, M.D. et al., "Complementary DNA Sequencing: Expressed Sequence Tags and Human Genome Project", Science, vol. 252, Jun. 21, 1991, pp. 1651–1656.

Anderson et al., "A homologue of the TNF receptor and its ligand enhance T–cell growth and dendritic–cell function", Nature, vol. 390, Nov. 13, 1997, pp. 175–179.

F.W. Fawthrop et al., "The Effect of Transforming Growth Factor βon the Plasminogen Activator Activity of Normal Human Osteoblast–like Cells and a Human Osteosarcoma Cell Line MG–63" J. Bone and Mineral Res. 7(12):1363–1371 (1992).

Fenton, A. J. et al., "Long–Term Culture of Disaggregated Rat Osteoclasts: Inhibition of Bone Resorption and Reduction of Osteoclast–Like Cell Number by Calcitonin and PTHrP[107–139]" J. Cellular Phys. 155:1–7 (1993).

George et al., Macromolecular Sequencing and Synthesis, New York, 1998, p. 127–149.

Kaji et al., "Insulin–like growth factor–I mediates osteoclast–like cell formation stimulated by parathyroid hormone", Journal of Cellular Physiology, vol. 172, No. 1, Jul. 10, 1997, pp. 55–62.

Kukita et al., "Osteoinductive factor inhibits formation of human osteoclast–like cells", Proc. Natl. Acad. Sci. USA, vol. 87, Jan. 29, 1990, pp. 3023–3026.

Lewis et al., "Cloning and expression of cDNAS for two distinct murine tumor necrosis factor receptors demonstrate one receptor is species specific", Proc. Natl. Aca. Sci. USA, vol. 88, 1991, pp. 2830–2834.

Rieger et al., Glossary of Genetics and Cytogenetics, Springer–Verlag, Berlin Heidlberg New York, 1976, p. 17.0.

Suda et al., "Modulation of Osteoclast Differentiation by Local Factors" Bone 117(2 Supp.):87S–91S (1995).

Wong et al., "TRANCE is a novel ligand of the tumor necrosis factor receptor family that activates c–Jun N–terminal kinase in T cell", J.Biol. Chem., vol. 272, No. 40, Oct. 28, 1997, pp. 24727–25408.

Yoneda, Toshiyuki, et al., "Sumarin Suppresses Hypercalcemia and Osteoclastic Bone Resorption in Nude Mice Bearing a Human Squamous Cancer", vol. 55, May 1, 1995, pp. 1989–1993, Cancer Research.

* cited by examiner

METHOD FOR DIAGNOSING BONE DYSBOLISM

This application is a 35 U.S.C. §371 filing of PCT/JP98/03421 filed on Jul. 31, 1998 which claims priority under 35 U.S.C. §119 to JP 276475/1997 filed on Sep. 24, 1997.

TECHNICAL FIELD

The present invention relates to a method of diagnosing metabolic bone diseases, especially osteoporosis and arthral diseases. In addition, the present invention relates to monoclonal antibodies used in the diagnosis and kits for diagnosis using the monoclonal antibodies. The present invention is useful as a method of diagnosing metabolic bone diseases, especially osteoporosis and arthral diseases, or as assay reagents for research use thereof.

BACKGROUND ART

Bone metabolism depends on integrated activity of osteoblasts that form bone and osteoclasts that resorb bone. In a healthy adult, the balance of bone formation and bone resorption is kept and the bone mass is maintained constant. Metabolic bone diseases are thought to develop by losing this balance. As metabolic bone diseases, osteoporosis, hypercalcemia, Pajet's disease, renal osteodystrophy, rheumatoid arthritis and osteoarthritis etc. are known. Osteoporosis is exemplified as a typical metabolic bone disease. Osteoporosis is thought to be a disease accompanied with decrease in bone mass and shows clinical symptoms, such as bone fracture or bone pain (lumbago and/or dorsalgia) caused by decrease in bone mass. Decrease in bone mass is induced by various causes such as aging after growing period, bone metastasis, or hyperthyroidism. As a method of diagnosing osteoporosis, bone mineral mass and/or bone density are determined by an apparatus to measure physical bone mass, such as X-ray diffraction (MD method), DPA (Dual photon absorptiometry), DEXA (Dual energy X-ray absorptiometry), CXD (Computed X-ray Densitometry) and low-frequency supersonic waves. The criterion of osteoporosis using these diagnostic methods is always rectified depending on technical revolution.

The risk of bone fracture in future might be surely predicted by decrease in bone mineral mass and/or bone density. However, decrease in bone mineral mass and/or bone density is not a sole risk factor of bone fracture and risk of bone fracture is thought to increase by phenomena accompanying with aging such as decrease in elasticity of collagen fiber, qualitative deterioration of bone structure, lowered muscular strength. At present risk factor except lowered muscular strength can not be measured non-invasively and non-invasive measurement is an important object to be solved in future. Further, decrease in bone mineral mass and/or bone density is just a result of losing the balance of bone metabolism and neither a cause of the disease or a diagnostic parameter thereof.

As supplement covering these defects of measurement of bone density, measurement of serum level and/or urinary excretion of factors regulating bone metabolism (parathyroid hormone (PTH), active form of vitamin $D_3$ and calcitonin etc.), various kinds of factor released from bone tissue accompanying with bone remodeling (bone alkaline phosphates, acid phosphatase, pyridinoline, deoxypyridinoline, type-I procollagen peptide, osteocalcin etc.) are tried to use to diagnose the disease. These factors would reflect of bone metabolic state at the time of measurement and are expected as an early parameter of bone loss and the extent thereof. However, as for these markers of bone metabolism, there are still problems, for example, they do not express local bone metabolic change, they can be affected by diet or circadian rhythm, so that changes in the level of these above factors do not necessarily reflect specific changes in bone metabolism. From these situations, development of highly specific and precise measurement of a novel marker involved in bone metabolism is expected for establishment of methods of suitable diagnosis, prevention and treatment of various kinds of metabolic bone diseases such as osteoporosis.

The present inventors found that osteoclastgenesis inhibitory factor (OCIF) was present in a culture medium of human fetal lung fibroblasts, IMR-90 (ATCC CCL186) and succeeded in isolation thereof. In addition, the inventors also succeeded in cloning of cDNA encoding this protein and confirmed the usefulness thereof as an agent for improving bone metabolism by evaluating pharmacological effect of recombinant OCIF (rOCIF) in vitro and in vivo (WO 96/26217). Further, the present inventors confirmed that administration of rOCIF significantly improved bone density and bone strength in various kinds of animal model of metabolic bone disease and that administration of a large amount of rOCIF also significantly increased bone mass and bone volume in a normal animal without was not any side-effect in the examination of various organs other than osseous tissue, hematology and clinical biochemistry and hemolytic cell. From the results of in vivo experiment, it was found that OCIF is a highly tissue-specific cytokine having an action only on osseous tissue. In addition, the present inventors confirmed that, in an animal cell, OCIF was secreted as homodimer form of OCIF with a molecular weight of about 120 kDa and the homodimer type of OCIF was converted into monomer form of OCIF with a molecular weight of about 60 kDa by protease processing. And as it was confirmed that both types of OCIF were present in a culture medium of human cell line (Tsuda et al. :Biochem. Biophys. Res. Commun. 234, 137–142)(1997)), it is expected that both types of OCIF are present in humor of mammal including human being.

Accordingly, for elucidating whether or not OCIF can be a novel marker of bone metabolism, it is necessary to study precisely the correlation between various kinds of metabolic bone diseases and the level of each type of OCIF or total concentration of both types of OCIF in one of patients with metabolic bone diseases. Therefore, an antibody recognizing equally both types of OCIF and an antibody recognizing only homodimer are required for the above purpose. Any anti-OCIF monoclonal antibody having such features has not been obtained yet.

DISCLOSURE OF THE INVENTION

Considering these situations, the present inventors eagerly studied and found monoclonal antibodies with markedly high affinity (dissociation constant thereof was less than $10^{-9}$ M) recognizing equally both of monomer- and homodimer-types of OCIF and monoclonal antibodies recognizing specifically homodimer type of OCIF. Further, the inventors constructed a highly sensitive enzyme immunoassay kit (sandwich ELISA) using these antibodies. As the results of measurement of serum concentration of OCIF in young adults, the aged, patients with osteoporosis, hyperthyroidism and various kinds of disease including cancer using the sandwich ELISA, a high inverse-correlation was found between serum concentration of OCIF and bone density. As the results of measurement of the concentration of OCIF in synovial fluid of patients with arthrosis such as rheumatoid arthritis, osteoarthritis, trauma and gouty seizure etc., OCIF concentration in synovial fluid of a patient with progressed joint destruction was found to be significantly low.

OCIF was found to be useful as a novel diagnostic marker of metabolic bone disease, because the determination of OCIF in serum and synovial fluid by the present sandwich ELISA makes it to precisely predict the dynamics of bone density and the progress of joint disruption, respectively, and thereby predict the decrease in bone mass and joint disruption at early stage of these bone decreases. Accordingly, an object of the present invention is to provide a method of diagnosing metabolic bone disease, especially osteoporosis, and joint destruction caused by rheumatism, characterized by determination of the concentration of human osteoclast-genesis inhibitory factor and monoclonal antibodies used therein and a kit for measurement of OCIF using the antibodies.

The present invention relates to a method of diagnosing metabolic bone disease by determination of the concentration of osteoclastgenesis inhibitory factor (OCIF) in sample humor.

The diagnosis of the present invention is especially useful for diagnosis of osteoporosis and arthrosis. As humor, serum or synovial fluid can be used. Diagnosis of osteoporosis can be carried out by determination of serum concentration of OCIF. And diagnosis of arthrosis can be carried out by determination of the concentration of OCIF in synovial fluid. Diagnosis by the present invention is especially useful for diagnosing osteoporosis. As a humor, serum or synovial fluid can be used.

In addition, the present invention relates to monoclonal antibodies used in the diagnosis. As monoclonal antibodies, a monoclonal antibody recognizing equally both of monomer- and dimer-types of OCIF and an antibody recognizing selectively only dimer type of OCIF can be exemplified. Further monoclonal antibodies include high affinity antibodies recognizing a different epitope and having dissociation constant of less than $2 \times 10^{-7}$ M with antigen.

Further, the present invention relates to a kit for OCIF determination comprising these monoclonal antibodies. The diagnostic method of the present invention can be carried out by taking humor such as blood (serum), synovial fluid from an object of diagnosis and measuring OCIF by a kit for OCIF determination using the above monoclonal antibodies.

The monoclonal antibodies can be obtained by the method described below. That is, as an antigen for immunization being necessary for preparation of anti-OCIF monoclonal antibody, human OCIF isolated from culture medium of human embryonic lung fibroblasts, IMR-90 (human embryonic lung fibroblast, ATCC CCL-186) according to a method described in WO96/26217 can be also used. Recombinant human OCIF can be also used. Recombinant human OCIF can be obtained by inserting cDNA of human OCIF into an expression vector in a conventional manner and expressing it in animal cell such as CHO cell, BHK cell and Namalwa cell etc., or insect cell followed by purification. According to the method of Tsuda et al. (Biochem. Biophys. Res. Common. 234, 137–142 (1997)), monomer- and dimer-types of OCIF can be purified by reverse-phase chromatography, respectively. Further, both types of OCIF can be respectively purified by a combination of SP-Sepharose, sulfated Cellurofine and resource S column chromatography in replace of reverse-phase chromatography. Spleen cells prepared from mammal immunized with the antigen or lymphocytes immunized in vitro can be fused with myeloma cell line to make a hybridoma. Using highly purified monomer- and homodimer-types of OCIF as antigens and culture media of the above hybridoma, the cell line can be established by screening hybridoma producing an antibody recognizing equally both types of OCIF or an antibody recognizing specifically only homodimer type of OCIF followed by cloning the hybridoma. Further, the aimed antibodies can be obtained by culturing the established and stable hybridoma.

When mammal is immunized for preparation of hybridoma, though animal species is not limited, small animal such as mice or rat is generally used. In immunization, OCIF as an antigen can be diluted in physiological saline solution to suitable concentration and the solution thereof can be administered intravenously or intraperitoneally, if necessary, Freund's complete adjuvant can be administered therewith, generally, 3–4 times at 1–2 weeks intervals in animal. On preparation of high affinity anti-OCIF monoclonal antibody (dissociation constant thereof is less than $2 \times 10^{-7}$), immunization can be carried out 3 times at intervals of one week and, further, immunization with antigen together with Freund's incomplete adjuvant can be carried out another 4 times at intervals of one week in order to obtain the aimed monoclonal antibody easily and to enhance titer of OCIF in blood as much as possible. Immunized animals described above can be anatomized 3 days after the final immunization and spleen can be dissected. Splenocytes can be used as immunized cell. As myeloma cell lines derived from mice to be hybridized with the immunized cell, p3/x63-Ag8, p3-U1, NS-1, MPC-11, SP-2/0, F0, p3x63 Ag8, 653 and S194 can be exemplified. Further, as a cell line derived from rat, R-210 can be exemplified.

To produce human antibody, human lymphocytes can be immunized in vitro and cell-fused with human myeloma cells or a human lymphocyte cell line transformed by EB virus. Fusion of immunized cells with myeloma cell line can be carried out according to a conventional method, for example, the method of Koehler and Milstein et al. (Koehler et al., Nature, 256, 495–497, 1975) but electric pulse method can be also used. Immunized lymphocytes and a myeloma cell line can be mixed at a usual rate in cell number and polyethylene glycol can be added to cell culture media used generally (not including Fetal calf serum, FCS) to carry out cell fusions and fused cells (hybridoma) can be selected by culturing in HAT selective medium containing FCS.

Hybridomas producing a monoclonal antibody recognizing equally both of monomer- and homodimer-types of OCIF and an antibody recognizing selectively homodimer type of OCIF can be selected according to a method of detecting antibody such as ELISA, plaque assay, ouchterlony method or agglutination method. ELISAs using purified monomer- and homodimer-types of OCIF can detect the object antibody very easily and precisely. It was difficult to obtain high affinity antibody (dissociation constant is less than $2 \times 10^{-7}$M) by usual solid phase ELISA. That is, when usual solid phase is used, culture media of hybridoma (50–100 $\mu$l) is placed into 96 well immunoplates coated with antigen (Nunc) to proceed the primary reaction and, then, enzyme labeling, for example, peroxidase (POD) labeled anti-mouse IgG antibody is added to proceed the secondary reaction. Then, the solution of enzyme substrate (50–100 $\mu$l) is added to each well in the immunoplates to complete enzymatic reaction and absorbance in each well is determined. Culture media of hybridoma showing high absorbance can be thought not only to produce a large amount of low affinity antibody but also to produce a high affinity antibody even if productivity of the antibody is low. It is not possible to determine which case is true.

Therefore, in the present invention, in order to recognize hybridoma producing a high affinity antibody, usual solid phase ELISA was improved as described below. That is, to each well of in 96 well immunoplates coated with an antigen, human serum or bovine serum was added, followed by the addition of a small amount of culture media of hybridoma to each well to proceed the primary reaction under the presence of about 80–90% of serum. Under such conditions, hybridomas producing antibodies with low affinity for the antigen, even if producing of the antibodies are high, can be excluded. Thus, the modified solid ELISA made it possible to selectively screen by hybridomas producing antibodies with high affinity for the antigen. Using the improved solid phase ELISA, hybridomas producing antibodies recognizing equally both of monomer- and homodimer-types of OCIF as antigens and another hybridomas producing antibodies recognizing specifically homodimer type of OCIF can be selected and stable hybridoma producing each antibody can be established by cloning 3–5 times by limited dilution method. Hybridoma established like this can be subcultured by culturing method usually used and preserved by freezing, if necessary. Hybridoma can be cultured by usual method and antibody can be recovered from the culture media. Further, antibody can be recovered from ascites derived from mammal in which hybridoma is implanted intraperitoneally. Antibody in culture media or in ascites can be purified by usual method of purifying antibody such as salting out, ion exchange or gel permeation chromatography, protein A or G affinity chromatography. Obtained antibody is an antibody recognizing equally both of monomer- and homodimer-types of OCIF and an antibody recognizing selectively homodimer type of OCIF. Each antibody can be used for measurement of the amount of OCIF (monomer type of OCIF+homodimer type of OCIF) and the amount of homodimer type of OCIF. These antibodies can be labeled by radioactive isotope or enzyme and used in radioimmunoassay (RIA) or enzymeimmunoassay (ELISA) to determine the amount of OCIF (the amount of monomer type of OCIF+homodimer type of OCIF) or the amount of homodimer type of OCIF only. Especially, the antibody of the present invention recognizing selectively homodimer type of OCIF can make it clear that there are different epitope(s) in monomer- and homodimer-types of OCIF and recognize the epitope present only in homodimer type of OCIF which is absent in monomer type of OCIF.

The amount of OCIF and the amount of homodimer type of OCIF can be determined by using an antibody obtained by the present invention recognizing equally both of monomer- and homodimer-types of OCIF as a solid phase antibody, and by using radioactive isotope or enzyme-labeled labeling antibody recognizing equally both of monomer- and homodimer-types and antibody recognizing selectively only homodimer type of OCIF with radioactive isotope or enzyme as secondary antibody, respectively.

Further, when only the amount of homodimer type of OCIF is wanted to determine, as a solid phase antibody, OI-26 antibody recognizing selectively homodimer type of OCIF as described in example 6 (table 1) and, as labeled antibody, OI-19 or OI-4 antibody recognizing equally both of monomer- and homodimer-types of OCIF can be also used. By using these assay systems, the amount of OCIF or only that of homodimer type of OCIF in body fluids such as blood, urine and synovial fluid etc. or in cell culture media can be determined.

A kit of the present invention comprises (i) any one of primary antibody and secondary antibody is OI-19 or OI-26 anti body, and (ii) the other antibody is OI-4 antibody and usual combination of reagents used in usual sandwich method. That is, an immunoassay kit comprises (1) primary antibody immobilized on insoluble carrier, (2) labeled secondary antibody, (3) solubilizer, (4) washing agent, and (5) substrate and reaction stopping reagent to determine enzymatic activity in the case of enzyme labeling. As insoluble carrier, polystyrene, polyethylene, polypropylene, polyester, polyacryronitrile, fluorinated resin, crosslinked dextran, polysaccharide, latex, latex polymer containing magnetic particles plated with metal etc., paper, glass, metal, agarose and combination of the above carries can be exemplified. As the shape of insoluble carrier, tray, sphere, fiber, stick, plate, container, cell, test tube, porous filter can be used. Further, as labeling materials used for preparation of labeled antibody, enzymes, fluorescent substances, luminescent substances and radioactive substances can be advantageously used. As enzymes, peroxidase, alkaline phosphatase, β-D-galactosidase, glucose oxidase, malate dehydrogenase, glucose-6-phosphate dehydrogenase, invertase can be used. As fluorescent substances, fluorescein isothiocyanate and phycobili-protein can be used. As luminescent substances, isolucinol and lucigenin can be used. And, as radioactive substances, $I^{125}$, $I^{131}$, $C^{14}$, $H^3$ can be exemplified. These above examples are merely examples and anything used in immunoassay can be used.

When a labeling material is enzyme, substrate and, if necessary, color developer can be used to determine enzymatic activity. When peroxidase is used as an enzyme, $H_2O_2$ is used as a substrate and, as color developer, 2,2'-azinodi [3-ethylbenzthiazoline sulfonic acid] ammonium salt (ABTS), 5-aminosalicylic acid, o-phenylenediamine, 4-aminoantipyrine, 3,3',5,5'-tetramethylbenzidine, homocevadillinic acid, and tyramine can be used.

And when alkaline phosphatase is used as an enzyme, o-nitrophenylphosphate and 4-methylumbelliferylphosphate can be used as a substrate. When β-D-galctosidase is used as an enzyme, fluoroscein-di-(β-D-galctopyranoside), 4-methylumbelliferyl-β-D-galctopyranoside can be used as a substrate.

As a solubilizer disclosed in (3) in the above immunoassay kit, any one used usually in immunoassay can be used, and for example, phosphate buffer solution, tris-HCl buffer solution, acetic acid buffer solution with pH of 6.0–8.0 can be respected as appropriate examples. Further, as a washing agent disclosed in (4), any one used generally in immunoassay can be used. For example, physiological saline solution, phosphate buffer solution, tris-HCl buffer solution and mixed solution thereof can be exemplified. Further, to the above washing agent, nonionic surfactant such as Triton X-100, Tween 20 or Brij 35 or ionic surfactant such as sodium dodesyl sulfate or CHAPS can be added.

BRIEF DESCRIPTION OF THE DRAWINGS

Explanation of Code
  RA: rheumatoid arthritis
  OA: osteoarthritis
  Tr: trauma
  G: gouty seizure

BEST MODE FOR PRACTICE OF THE INVENTION

The present invention will be described in more detail by showing examples. However, these are merely examples and the scope of the present invention will not be limited by these examples.

EXAMPLE 1
Purification of Monomer Type of OCIF or Homodimer Type of OCIF as an Antigen OCIF-producing CHO cells described in WO96/26217 were seeded in EX-CELL 301 medium (JRH Bioscience) at a cell density of $1 \times 10^5$ cells/ml and cultured at 37° C. for 7 days using a jar for cell culture (2 liters container). To the obtained culture medium, CHAPS (3-[(3-cholamidopropyl)-dimethylammonio-]-1-propanesulfonate, Sigma) was added to a concentration of 0.1%. After pH of the medium was adjusted to 6.0 by acetic acid, the medium was filtered through 0.22 μm filter (milidisk, Millipore). The culture medium was loaded on a SP sepharose HP column (2.6×10 cm, Pharmacia) equilibrated with 50 mM bis-tris-HCl buffer solution containing 0.1% CHAPS. After washing the column with the same buffer solution, the column was developed with a linear gradient from 0 to 1 M NaCl for 100 minutes at a flow rate of 4 ml/min. and the elute was fractionated into 8 ml each. According to the method described in WO96/26217, OCIF activity in each fraction was determined, so that OCIF fraction was obtained. After the OCIF fraction was diluted 10-fold with 50 mM bis-tris-HCl buffer solution, pH 6.0 containing 0.1% CHAPS, it was loaded on a sulfate-cellurofine column (2.6×10 cm, Seikagaku-kogyo) equilibrated with 50 mM bis-tris-HCl buffer, pH 6.0. The column was washed with 50 mM bis-tris-HCl buffer solution at pH 6.0 containing 0.1% CHAPS, followed by developing with linear gradient from 0 to 1.5 M NaCl for 100 minutes at flow rate 4 ml/min. and fractionating into 8 ml each. OCIF activity in each fraction was determined as described above.

A portion of each fraction was subjected to SDS-PAGE under non-reducing conditions and fractions having OCIF activity and molecular weight of 60 kDa were collected and the OCIF pool was named fraction 1. In addition, fractions having OCIF activity and showing molecular weight of 120 kDa under non-reducing conditions were collected and the OCIF pool was named fraction 2. Fraction 1 and fraction 2 were diluted 10-foled with 50 mM tris-HCl buffer, pH 7.0, containing 0.1% CHAPS, respectively and each fraction was loaded on a RESOURCE S column (0.64×3 cm, Pharmacia) equilibrated with 50 mM tris-HCl buffer, pH 7.0, containing 0.1% CHAPS. After washing the column with 10 mM sodium phosphate buffer, pH 7.0 containing 0.01% polysorbate, the column was developed with a linear gradient from 0 to 0.6 M NaCl for 15 minutes at flow rate of 1 ml/min. and fractionating into 0.5 ml each. OCIF activity in each fraction of fraction 1 and fraction 2 was determined as described above and fractions having OCIF activity were collected, so that monomer type of OCIF from fraction 1 and homodimer type of OCIF from fraction 2 were obtained.

EXAMPLE 2
Immunization of Mice and Preparation of Hybridoma

Monomer- and homodimer-types of OCIF purified as described in example 1 were dissolved in physiological saline solution to concentration of 100 μg/ml, respectively. To a mixture each containing equal amount of both types of OCIF prepared as above, the same volume of Freund's complete adjuvant was added. The mixed solution was emulsified well and administered intraperitoneally (200 μl/mouse) to Balb/c mice 3 times at intervals of one week to immunize mice. Then, to a mixture containing 25 μg/ml of each both types of OCIF, the same volume of Freund's incomplete adjuvant was added to make an emulsion, 200 μl of which was administered per mouse to the above Balb/c mice 4 times at intervals of one week.

One week after the 4th booster immunization, 100 μl of a mixed solution containing 100 μg/ml of each both types of OCIF was intravenously administered to Balb/c mice. Three days after the final immunization, spleen was dissected and spleen cells were isolated and fused with mouse myeloma cells, P3x63-AG8.653 (ATCC CRL-1580), according to the conventional method (Koehler, G. and Milstein, C., Nature, 256.495 (1975)). After cell fusion, cell suspension was cultured in HAT medium containing hypoxanthine, aminopterin and thymidine for 10 days. After hybridoma appeared in replace of myeloma cells, cell culture was kept on culturing by changing culture medium into HT medium excluding aminopterin from HAT medium.

EXAMPLE 3
Selection and Cloning of Hybridoma

Ten days after the cell fusion, hybridomas appeared. Hybridoma producing high affinity antibody recognizing equally both of monomer- and homodimer-types of OCIF and hybridomas producing antibody recognizing selectively homodimer type of OCIF were screened. That is, monomer- and homodimer-types of OCIF were dissolved in 0.1 M sodium bicarbonate (pH 9.6) to a concentration of 5 μg/ml, respectively and 50 μl of each antigen solution was added to each well in 96 well immunoplates (Nunc) and the plates were kept at 4° C. overnight to coat each well with each antigen. Antigen solution in each well was discarded and each well was washed with phosphate buffered saline containing 0.1% polysorbate 20 (PBS-P) and 40 μl of bovine fetal serum was added to each well.

Then, 10 μl of conditioned medium of hybridoma was added to each well and then the plates were incubated under 80% serum concentration at room temperature for 2 hours. After the incubation, plates were washed with PBS-P and 50 μl of peroxidase labeled anti-mouse IgG (KPL) diluted 5000-fold with physiological saline solution containing 25% BLOCKACE was added to each well and the plates were incubated at room temperature for 2 hours. After washing the plates with PBS-P, 50 μl of enzyme substrate solution (TMB, ScyTek) was added to each well for color developing. Subsequently the enzymatic reaction was terminated by adding 50 μl of stopping reagent, (ScyTek). Hybridomas producing antibodies were screened by determing absorbance at 450 nm of each well using microplate reader (an immunoreader NJ2000, Nihon-intermed). Hybridomas showing high absorbance and producing antibody recognizing equally both of monomer- and homodimer-types of OCIF, and hybridomas showing high absorbance and producing antibody recognizing selectively homodimer type of OCIF were screened, respectively. Stable hybridoma clone producing hybridoma cell line was established by repeating cloning 3–5 times from each hybridoma by limiting dilution method. Among hybridomas producing antibodies, hybridomas with high productively of the object antibodies were selected.

Thus, the hybridomas, OI-19 and OI-4 which produced the antibodies, OI-19 and OI-4, respectively, recognizing equally both of monomer- and homodimer-types of OCIF were obtained. In addition, the hybridoma, OI-26 which produced OI-26 antibody, OI-26, recognizing selectively homodimer type of OCIF was obtained. These hybridomas were deposited at National Institute of Bioscience and Human-Technology Agency of Industrial Science and Technology and the deposit number for OI-4, OI-19 and OI-26 was FFERM BP-6419, FERM BP-6420 and FERM BP-6421, respectively.

EXAMPLE 4

Production and Purification of Monoclonal Antibody

Hybridoma producing high affinity antibody recognizing equally both of monomer- and homodimer-types of OCIF and hybridoma producing antibody recognizing selectively homodimer type of OCIF obtained in example 3 were cultured, respectively, and $1 \times 10^6$ cells of hybridoma per mouse were intraperitoneally administered to Balb/c mice in which pristine (Aldrich) had been administered. Two weeks after administration, accumulated ascites containing monoclonal antibody of the present invention was collected. Purified antibody was obtained by protein A column (Pharmacia) chromatography.

EXAMPLE 5

Determination of Dissociation Constant (Kd Value) of Monoclonal Antibody

According to the method of Betrand Friguet (Journal of Immunological Methods, 77, 305–319, 1986), dissociation constant of monoclonal antibody was determined. That is, purified antibody obtained in example 4 was diluted in 0.2 M tris-HCl pH 7.4 (first buffer) containing 40% BLOCK-ACE (Snow Brand Milk Products) and 0.1% polysorbate 20 to a concentration of 5 ng/ml. To the above solution, the same volume of 6.25 ng/ml-10 μg/ml of purified monomer type of recombinant OCIF or homodimer type of recombinant OCIF which was obtained in example 1, diluted with the first buffer was mixed and the mixture was kept it at 4° C. for 15 hours, so that OCIF bound to monoclonal antibody. At 15 hours after then, dissociation constant of monoclonal antibody against monomer type of OCIF or homodimer type of OCIF was determined by measuring antibody unbound to OCIF using solid phase ELISA in which monomer type of rOCIF or homodimer type of rOCIF (10 μg/ml, 100 μl/well) was immobilized.

EXAMPLE 6

Assay of Class and Subclass of Monoclonal Antibody

The class and the subclass of monoclonal antibody of the present invention was assayed using immunoglobulin class and subclass assay kit (Amersham). The assay was carried out according to the protocol directed in a kit. The results obtained in example 5 and 6 were shown in table 1.

TABLE 1

| Antibody | subclass | Dissociation constant (for monomer) | dissociation constant (for dimer) |
|---|---|---|---|
| OI-4 | IgG$_1$ (κ) | $7.3 \times 10^{-10}$ | $9.9 \times 10^{-12}$ |
| OI-19 | IgG$_1$ (κ) | $7.0 \times 10^{-10}$ | $1.2 \times 10^{-11}$ |
| OI-26 | IgG$_1$ (κ) | — | $1.5 \times 10^{-7}$ |

From these results, the antibodies, OI-4 and OI-19, were found to be antibody recognizing equally both of monomer- and homodimer-types of OCIF and antibody OI-26 was found to be antibody recognizing selectively only homodimer type of OCIF. Further, all antibodies belonged to IgG1 and were found to be antibodies with extremely high affinity having dissociation constant of less than $2 \times 10^{-7}$ M for monomer- and homodimer-types of OCIF.

EXAMPLE 7

Determination of OCIF by ELISA

Sandwich ELISA was constructed by using 3 kinds of antibody obtained as described above, that is, antibody OI-4, OI-26 and OI-19 as immobilized antibody and labeled antibody. Labeling antibody was carried out using maleimide activated peroxidase kit (Pias). The Antibody, OI-19 as a primary antibody in the case of ELISA measuring both of monomer- and homodimer-types of OCIF or the antibody, OI-26 as a primary antibody in the case of ELISA measuring selectively homodimer type of OCIF was dissolved in 0.1 M sodium bicarbonate (pH 9.6) to a concentration of 10 μg/ml, respectively, 100 μl of which was added to each well in 96 well immunoplates (Nunc) and the plates were kept at 4° C. overnight to immobilize antibody onto each well. The solution in each well was discarded and 300 μl of 50% BLOCK-ACE (Snow Brand Milk Products) was added to each well to block at room temperature for 2 hours. After blocking, plates were washed with phosphate buffered saline (PBS-P) containing 0.1% polysorbate 20. Monomer- and homodimer-types of OCIF were dissolved in 0.2 M tris-HCl (pH 7.4) containing 40% BLOCKACE (Snow Brand Milk Products) and 0.1% polysorbate 20 (primary buffer), respectively, and then diluted to prepare each type of OCIF solutions with various concentrations.

To each well, 100 μliter of the solutions of monomer type or homodimer type of OCIF with various concentrations was added to react at room temperature for 2 hours. Two hours after, plates were washed with PBS-P and POD-labeled OI-4 antibody diluted in 0.1 M tris-HCl (pH 7.4) containing 25% BLOCKACE and 0.1% polysorbate was added to each well in the plates as an antibody recognizing equally both of monomer- and homodimer-types of OCIF and the plates were allowed to stand at room temperature for 2 hours. Plates were washed with PBS-P and 100 μl of enzyme substrate solution 3,3'-5-5'-tetramethylbenzoide (TMB, ScyTek) was added to each well. After developing, 100 μl of stopping reagent, (ScyTek) was added to each well to stop enzymatic reaction. Absorbance at 450 nm of each well was determined using a microplate reader. The results in the case of using the antibody, OI-19, recognizing equally both of monomer- and homodimer-types of OCIF as a primary antibody was shown in FIG. 1 and the results in the case of using the antibody, OI-26, recognizing selectively homodimer type of OCIF as a primary antibody was shown in FIG. 2.

Figure 1:
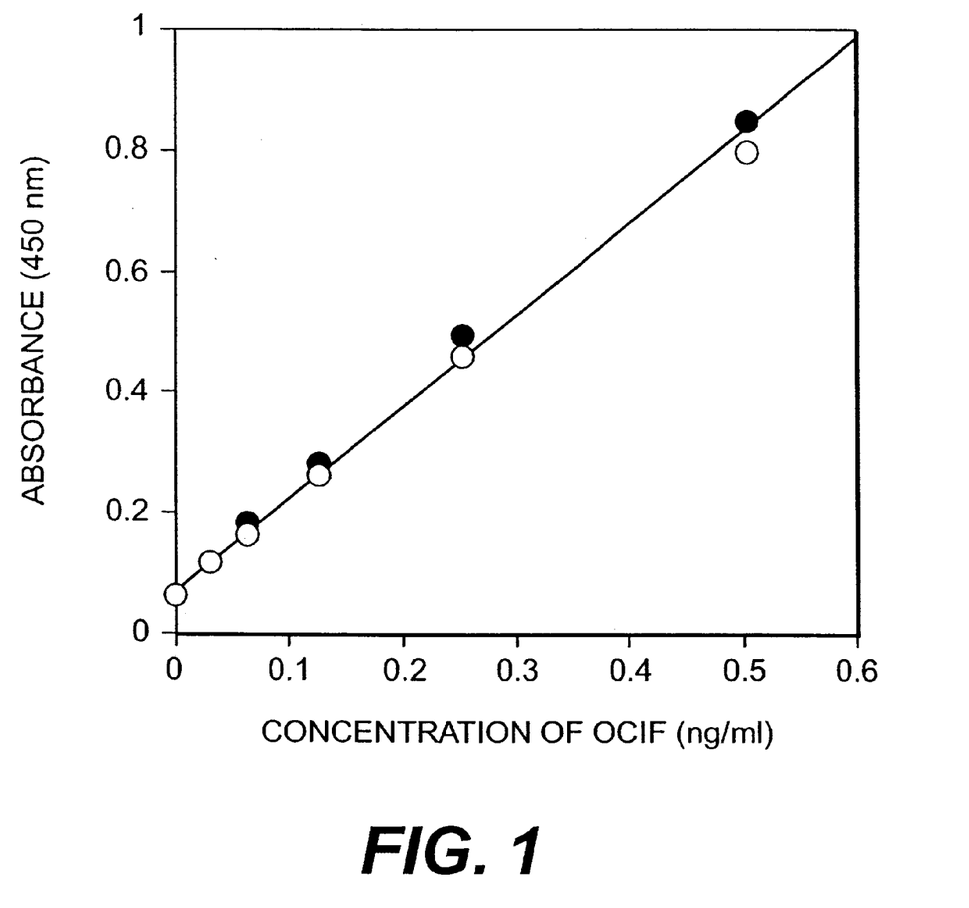
FIG. 1 shows standard curve of ELISA using OI-19 antibody and OI-4 antibody in example 7.
Explanation of Code
○: homodimer type of OCIF
●: monomer type of OCIF
Figure 2:
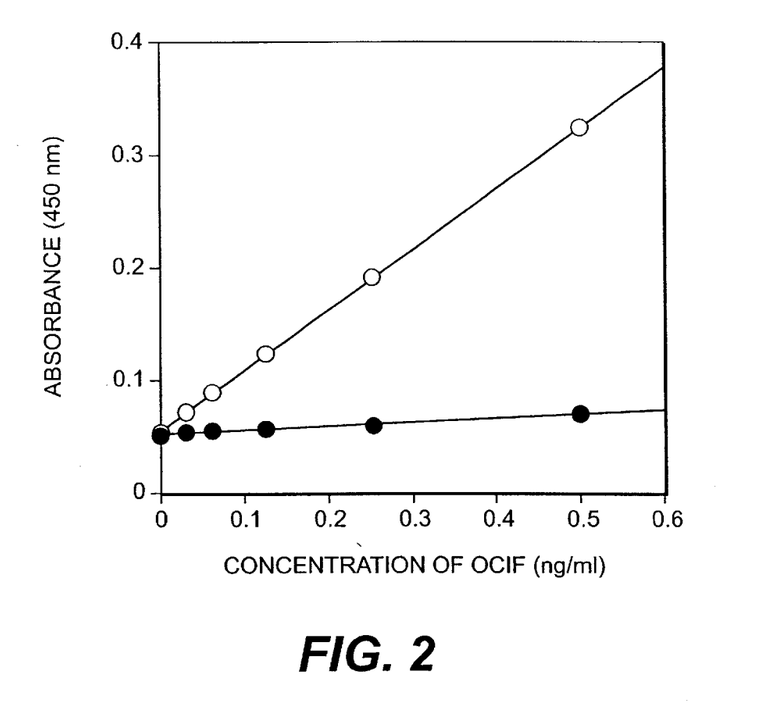
FIG. 2 shows the calibration of ELISA using OI-26 antibody and OI4 antibody in example 7.
Explanation of Code
○: homodimer type of OCIF
●: monomer type of OCIF

As a result, as shown in FIG. 1, detection sensitivity of sandwich ELISA was about 25 pg/ml and found to be able to determine extremely small amount of OCIF when the antibody, OI-19 recognizing equally both of monomer- and homodimer-types of OCIF was used as an immobilized antibody and the antibody, OI-4 recognizing equally both types of OCIF was used as a POD-labeled antibody. Further, as shown in FIG. 2, detection sensitivity of sandwich ELISA was 50 pg/ml and found to be able to detect selectively homodimer type of OCIF with high sensitivity when the antibody, OI-26, recognizing selectively homodimer type of OCIF was used as an immobilized antibody and the antibody, OI-4, recognizing equally both of monomer- and homodimer-types of OCIF was used as a POD-labeled antibody.

EXAMPLE 8

Determination of Serum OCIF in Healthy Persons and in Patients with Osteoporosis Serum concentration of OCIF in healthy persons and in patients with osteoporosis (based on the criterion made by Japanese Society for Bone and Mineral Research) was determined using a partly improved ELISA system of OCIF (monomer type of OCIF+homodimer type of OCIF) described in example 7. That is, for determination of OCIF (monomer type of OCIF+homodimer type of OCIF), the antibody, OI-19, recognizing equally both types of OCIF was immobilized onto 96 well immunoplate as described in example 7 and 50 $\mu$l of the first buffer (0.2 M tris-HCl, pH 7.4 containing 40% BLOCKACE and 0.1% polysorbate 20) containing 20 $\mu$g/ml purified mouse IgG was added to each well. Subsequently, 50 $\mu$l of human serum diluted 4-fold with the first buffer was added to each well and the plates were allowed to stand at room temperature for 2 hours. After the plates were washed with PBS-P 6 times, 100 $\mu$l of the solution of POD-labeled antibody, OI-4, recognizing equally both types of OCIF diluted 3000 times with secondary buffer (0.1 M tris-HCl, pH 7.4 containing 25% BLOCKACE and 0.1% polysorbate 20) containing 10 $\mu$g/ml purified mouse IgG was added to each well and the plates were allowed to stand at room temperature for 2 hours. The plates were washed 6 times with PBS-P and 100 $\mu$l of enzyme substrate solution (TMB, SciTech) was added to each well. The plates were allowed to stand at room temperature for 20 minutes to proceed enzymatic reaction and the reaction was stopped by adding 100 $\mu$l of stopping reagent (ScyTek) to each well. Absorbance at 450 nm of each well was determined using a microplate reader. As for the first buffer containing the known amount of OCIF, the same procedure as the above was taken and standard curve of OCIF was made as in FIG. 1. Serum concentration of OCIF was determined from absorbance of serum sample.

Figure 3:
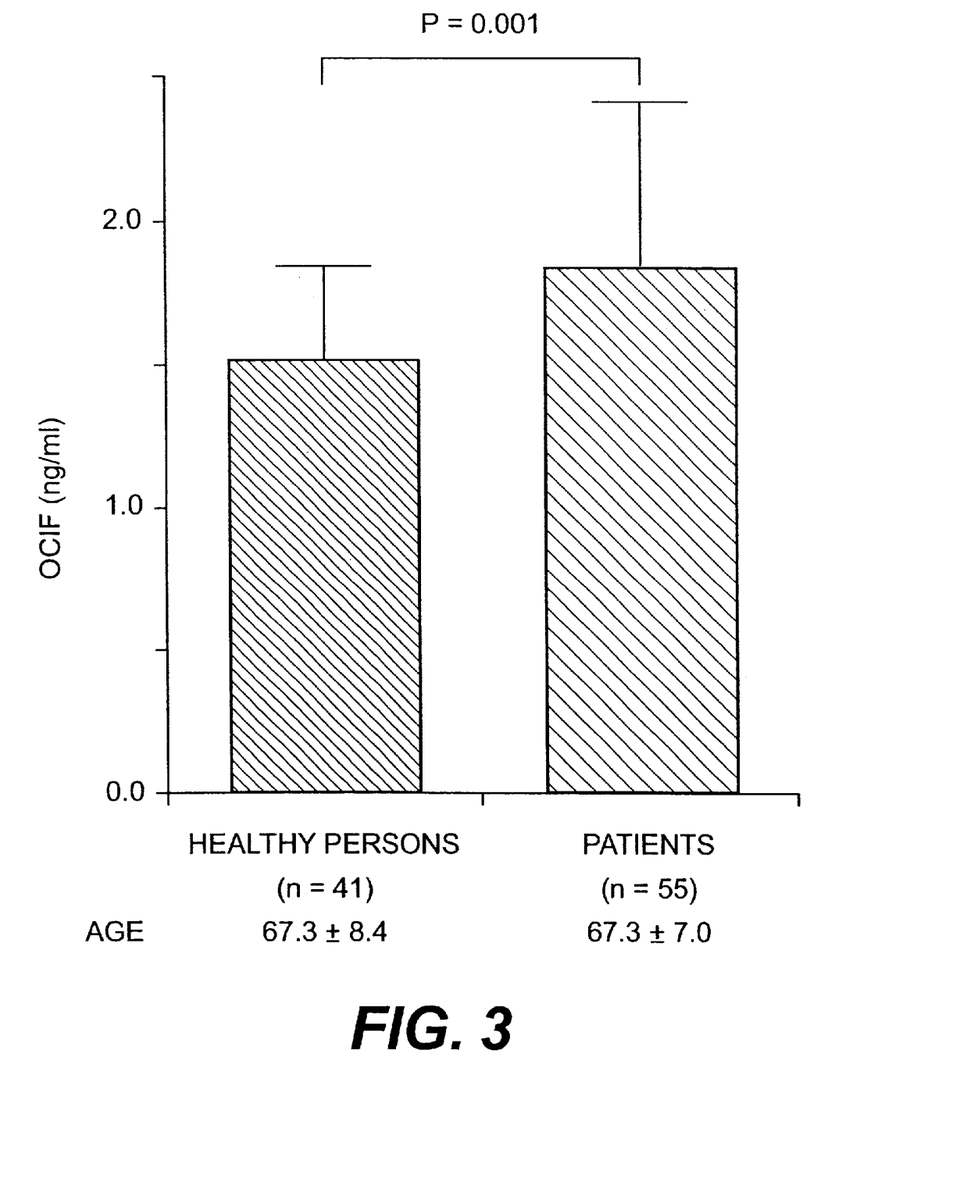
FIG. 3 shows the blood concentration of OCIF in patients with osteoporosis and in healthy persons in example 8.

The results of determination of serum concentration of OCIF (monomer type of OCIF+homodimer type of OCIF) in healthy persons and that in patients with osteoporosis were shown in FIG. 3. Statistical analysis of significant difference of the results in FIGS. 3–5 was carried out by Student's non-paired t test. As the results, there was a significant difference between serum concentration of OCIF (monomer type of OCIF+homodimer type of OCIF) in healthy persons and that in patients with osteoporosis. Serum concentration of OCIF in patients with osteoporosis was higher than that in healthy persons. Accordingly, OCIF was found to be a novel marker of diagnosing osteoporosis because pathogenesis of osteoporosis could be followed by determination of serum concentration of OCIF.

Figure 4:
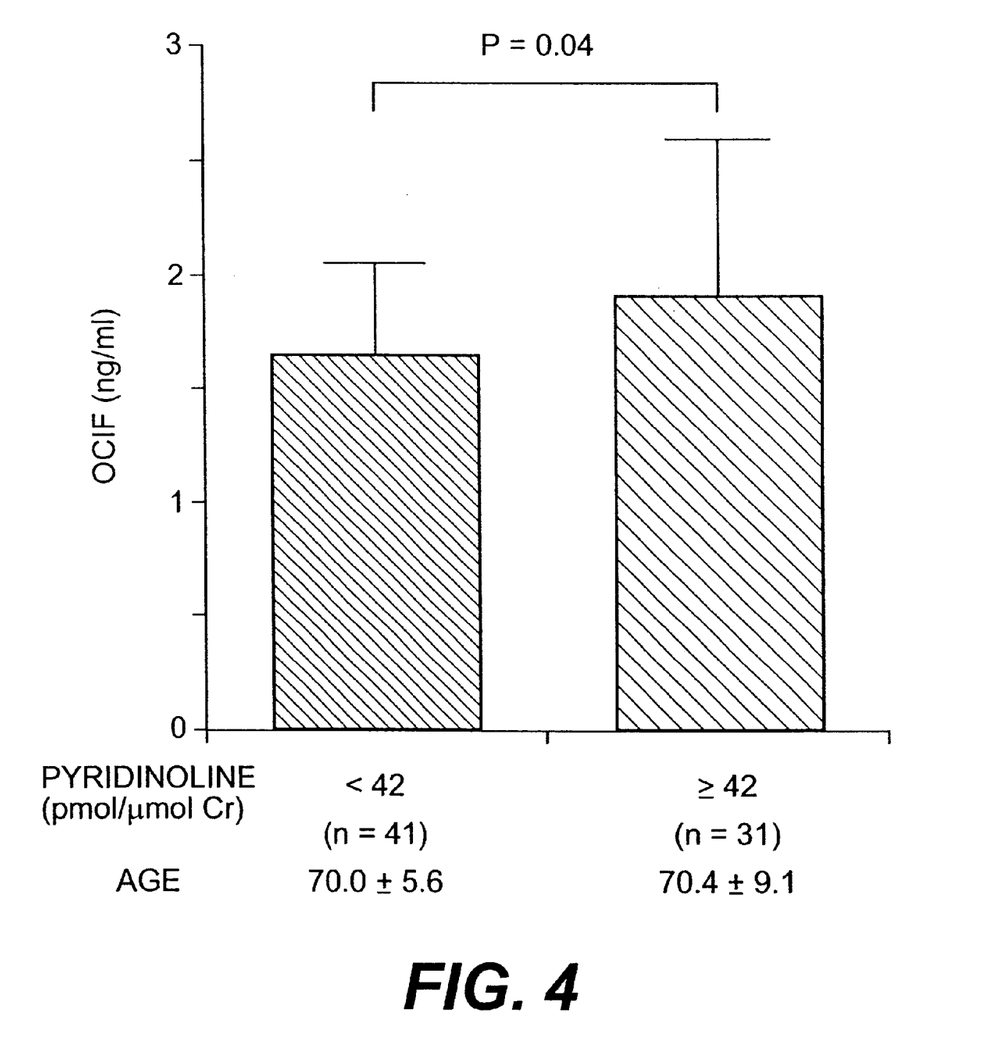
FIG. 4 shows the correlation between the urine concentration of pyridinoline and the blood concentration of OCIF in example 8.
Figure 5:
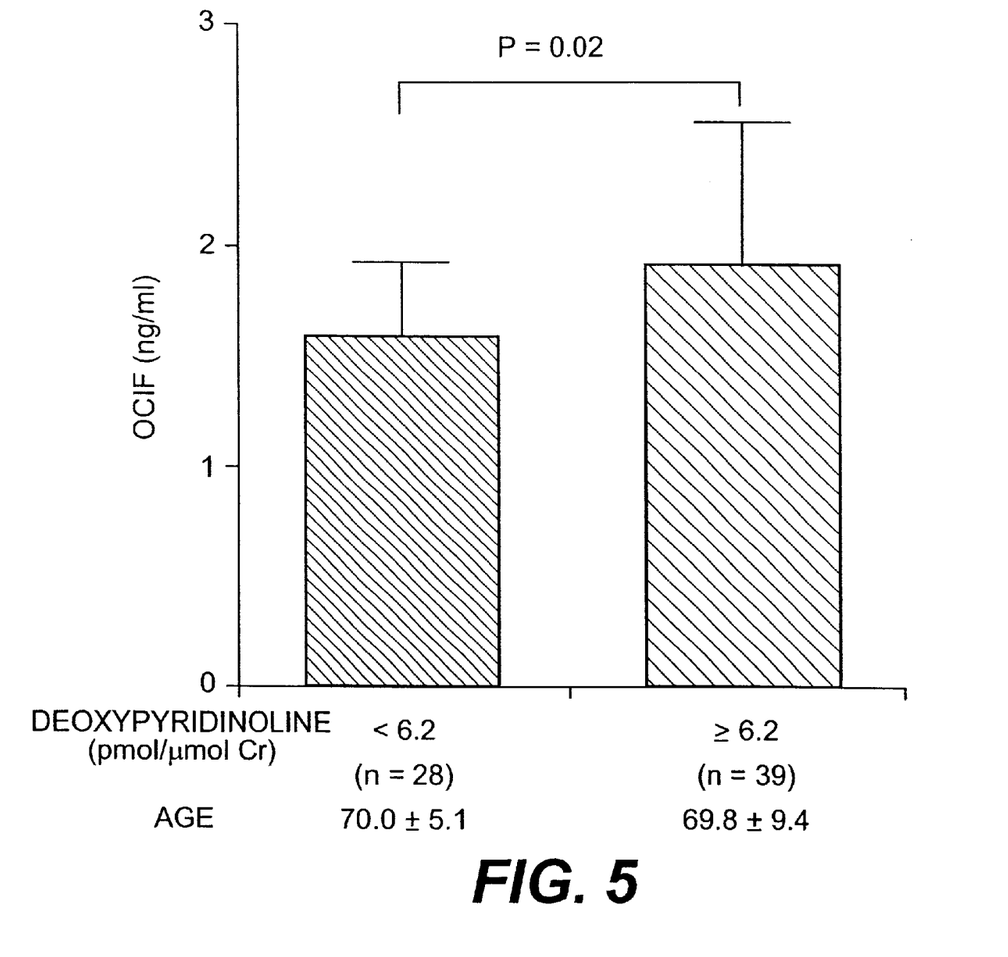
FIG. 5 shows the correlation between the urine concentration of deoxypyridinoline and the blood concentration of OCIF in example 8.

In addition, relationships between serum OCIF (monomer type of OCIF+homodimer type of OCIF) and urine pyridinoline concentrations, and between serum OCIF and urine deoxypyridinoline concentrations in healthy volunteers and patients with osteoporosis are shown in FIGS. 4 and 5, respectively. Pyridinoline concentration of 42 pmol/$\mu$mol Cr (the amount of pyridinoline pmol per creatinine 1 mol) and deoxipyridinoline concentration of 6.2 pmol/$\mu$mol Cr are the upper limit of normal level in Japanese.

From the results, serum concentration of OCIF in patients showing higher concentration of pyridinoline and/or deoxypyridinoline was significantly higher. Pyridinoline and deoxypyridinodine are cross-linked molecules of collagen, produced in bone substrate after incorporation of collagen into bone substrate, and released by bone destruction which is caused by bone resorption. These molecules are thought to be a highly specific marker of bone resorption and used widely for evaluation of clinical object. Since correlation between OCIF concentration and the two marker was recognized, serum concentration of OCIF was found to be useful as a marker of bone metabolism.

EXAMPLE 9

Determination of OCIF Concentration in Synovial Fluid of Patients with Arthrocele Synovial fluid samples were taken from patients with rheumatoid arthritis (RA, 43 cases), osteoarthritis (OA, 6 cases), Trauma (Tr, 3 cases) and gouty seizure (G, 6 cases) who visited hospital for treatment of arthrosis, were diagnosed as clear arthrocele and agreed with informed consent. OCIF concentration in the synovial fluid was measured by a partly improved method of ELISA system of OCIF (monomer type of OCIF+homodimer type of OCIF) described in example 8. That is, after synovial fluid was diluted 16-fold with the first buffer, 50 $\mu$l of which was added to each well in 96 well immunoplates immobilized antibody OI-19. Other procedures than the above were the same as those in example 8.

Figure 6:
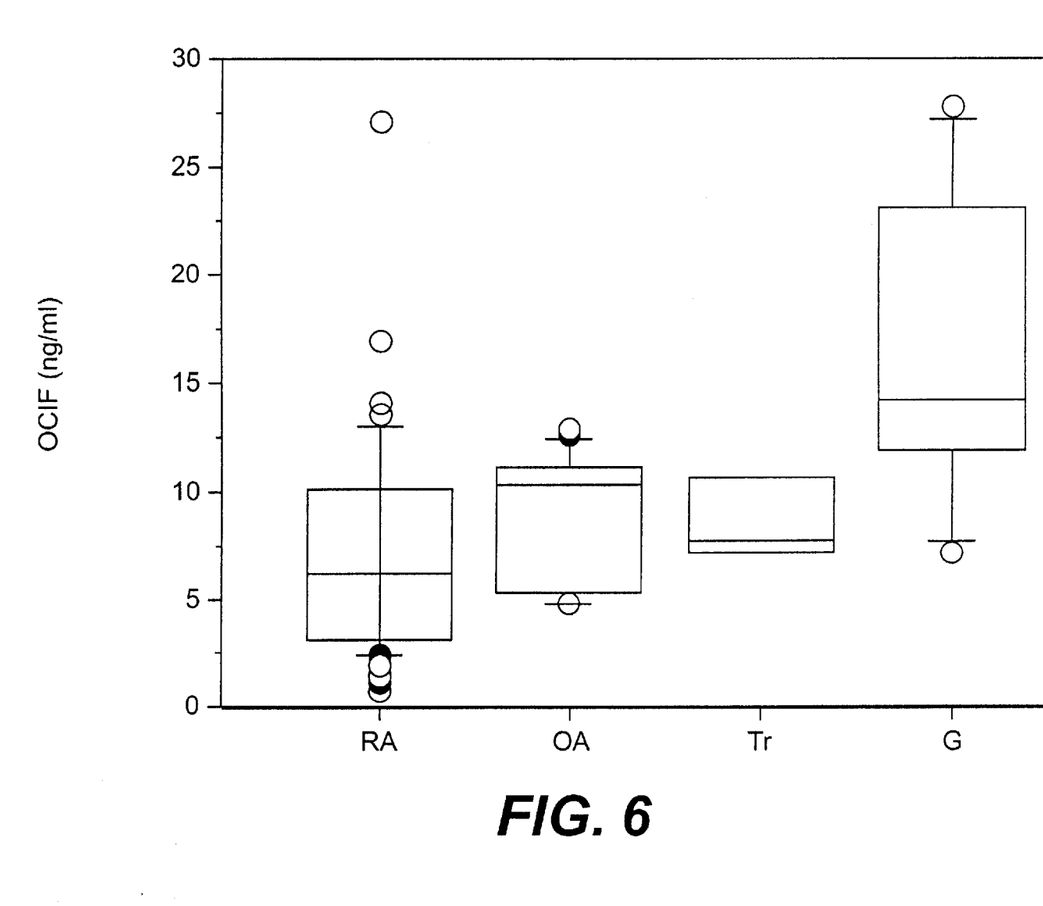
FIG. 6 shows the concentration of OCIF in synovial fluid of patients with arthrocele in example 9.

Examination results of OCIF (monomer type of OCIF+ homodimer type of OCIF) concentration in synovial fluid of patients with arthrocele were shown in FIG. 6. For statistical analysis of data shown in FIG. 6, Kruskal-Wallis Test and Mann-Whitney Test were carried out. From the results, OCIF concentration in synovial fluid of patient with rheumatoid arthritis was significantly lower than that of patient with gouty seizure (p=0.0023). Further, while the lowest value of OCIF concentration in synovial fluid of patients with osteoarthritis (6 cases) was 4.79 ng/ml, the number of patients with rheumatoid arthritis showing less than 4.0 ng/ml of OCIF concentration in synovial fluid was 15 cases among 43 cases.

From these results, it was suggested that deficiency of OCIF could not suppress formation and activity of osteoclasts in patients with rheumatoid arthritis showing lower OCIF concentration in synovial fluid. OCIF-ELISA was found to be useful for diagnosis of pathogenesis rheumatoid arthritis (RA), osteoarthritis (OA), Trauma (Tr), gouty seizure (G).

EXAMPLE 10

Correlation Between OCIF Concentration in Knee Joint Humor of Patient with Rheumatoid Arthritis (RA) and Pathogenesis In order to study the correlation between OCIF concentration in synovial fluid and progress of joint destruction, retrospective cohort study was carried out in 2 patients with rheumatoid arthritis.

Case 1, 66 Years Old, Male

He had subjective symptom of multiarticular pain at his 50 years old in 1982. In 1983, he visited a hospital and was diagnosed as RA based on classification criterion of RA of American College of Rheumatology. After that, since it remitted by administration of anti-rheumatoid agent (Mercaptase), administration the an anti-rheumatoid agent was stopped. In 1990, because RA recurred, administration of the anti-rheumatoid agent was restarted. On Mar. 18, 1992, his right knee joint swelled and synovial fluid was taken by puncture. The OCIF concentration in synovial fluid was 23.6 ng/ml, which was high level (The median value of OCIF concentration of 43 RA patients was 6 ng/ml). Plasma CRP at that time was 5.4 mg/dl, which clearly suggested that he had also inflammation. CRP did not become negative and kept around 3 mg/dl until 1997. Knee X-p was observed from 1983 to 1997 and main symptom was osteoarthritis. Bone erosion was not observed in digit joint of hand and hand joint.

Case 2, 60 Years Old, Female

She had subjective symptom of multiaricular pain in 1987 (49 years old). On Aug. 17, 1993 she visited a hospital and was diagnosed as RA based on classification criterion of RA of American College of Rheumatology. At that time, her right knee joint swelled and synovial fluid was taken by puncture. OCIF concentration in synovial fluid was 3.0 ng/ml, which was low level and plasma CRP was 13.7 mg/dl, which showed that she had inflammation. Since then, CRP gradually decreased by administration of anti-rheumatoid agent (Methotrexate) to a level of 4.1 mg/dl on Mar. 18, 1994 and to a level of 1.1 mg/dl on June 27 in the same year. However, according to Laresen classification (Laresen A. et al., Acta Radiol. Diag. 18, 481–491, 1977), knee X-p become worse and worse, that is, grade III on Sep. 1, 1993, grade IV on Mar. 18, 1994 and grade V on June 27 in the same year, which showed that joint destruction progressed clearly. And operation of replacing artificial joint on Oct. 4, 1994 was carried out.

From the results of determination of OCIF concentration in synovial fluid of the above 2 cases, that is, one with mild progress of joint destruction and another with advanced joint destruction, determination of OCIF concentration in synovial fluid was found to be useful for evaluation of risk rate of joint destruction by rheumatism and evaluation of therapeutic effect on joint destruction.

EXAMPLE 11

Assay Kit for Determination of Monomer- and Homodimer-Types of OCIF (80 Samples)
1) 96 well plate immobilized the antibody, OI-19 and subsequently blocked with BLOCKACE according to the method described in example 7: one plate
2) OI-4 antibody labeled with POD according to the method in example 7:10 µl (1000-fold dilution)
3) standard recombinant OCIF (monomer type): 0.5 ng/ml 400 µl
4) solution for dilution of sample (0.01% Tween 20 and 0.2 M tris-HCl buffer containing 40% BLOCKACE, pH 7.4): 10 ml
5) solution for dilution of labeled antibody (0.1M tris-HCl buffer containing 0.01% Tween 20 and 25% BLOCKACE, pH 7.4): 10 ml
6) solution for washing 96 well plate (PBS(-) containing 0.1% Tween 20): 1 liter
7) substrate solution for measurement of labeled enzyme activity (TMB solution) and reaction stopping reagent (TMB stop reagent): 10 ml, each Assay Kit for Determination of Dimer Type of OCIF (80 Samples)
1) 96 well plate immobilized the antibody, OI-26 and subsequently blocked with BLOCKACE according to the method described in example 7: one plate
2) OI-4 antibody labeled with POD according to the method in example 7:10 µl (1000-fold dilution)
3) standard recombinant OCIF (dimer type): 0.5 ng/ml 400 µl
4) solution for dilution of sample (0.01% Tween 20 and 0.2 M tris-HCl buffer containing 40% BLOCKACE, pH 7.4): 10 ml
5) diluted solution of labeled antibody (0.1 M tris-HCl buffer solution containing 0.01% Tween 20 and 25% BLOCKACE pH 7.4): 10 ml
6) solution for washing 96 well plate (PBS(-) containing 0.1% Tween 20): 1 liter
7) substrate solution for measurement of labeled enzyme activity (TMB solution) and reaction stopping reagent (TMB stop reagent): 10 ml, each Assay Method (Kit 1 and Kit 2)

To each well in the plate 1), 100 µl of sample diluted with the solution 4) and 100 µl of serially diluted standard recombinant human OCIF 3) with the solution 4) are added, respectively. After it is kept at room temperature for 2 hours, each well is washed 5–6 times with 300 µl of the solution 6). For this washing procedure, an automatic plate washer can be used. To each well in the plate after washing, 100 µl of POD-labeled OI-4 antibody 2) diluted 1000-fold with the solution 5) is added, and the plate is kept at room temperature for 2 hours. Each well in the plate is washed 5–6 times with the solution 6). For this washing procedure, an automatic plate washer can be used. To each well, 100 µl of enzyme substrate solution 7) is added, and the plate is kept at room temperature for 20–30 minutes. Subsequently, the enzymatic reaction is stopped by the addition of 100 µl of reaction stopping reagent 7).

Absorbance at 450 nm of each well is determined by a microplate reader. Using absorbance at 450 nm in the case of adding standard recombinant human OCIF 3) diluted serially to each well, standard curve of recombinant human OCIF is made. OCIF concentration of each sample can be determined using this standard curve.

Industrial Utility

By determining the concentration of human osteoclastgenesis inhibitory factor in humor (blood, synovial fluid, etc.) according to the method of the present invention, diagnosis of metabolic bone diseases, especially osteoporosis and arthrosis can be carried out easily and precisely. For diagnosis of the present invention, because the aforementioned monoclonal antibodies and assay kits for OCIF using the monoclonal antibodies are used, diagnosis of metabolic bone diseases, especially osteoporosis and arthrosis can be carried out easily and precisely as mentioned above. The present invention is useful for a method of diagnosing metabolic bone diseases, especially osteoporosis and arthrosis or for an assay reagent for research thereof.

Reference to Microorganism
Name and Address of Depository Authority to Which Said Organisms of the Present Invention Were Deposited
Name: National Institute of Bioscience and Human-Technology
Agency of Industrial Science and Technology
Ministry of International Trade and Industry
Address: 1–3, Higasi 1-chome, Tsukuba-shi, Ibaraki-ken, Japan
Date of deposition thereof to the depository authority: Oct. 16, 1997
Depository Number Given by the Depository Author: FERM BP-6419
Name and Address of Depository Authority to Which Said Organisms of the Present Invention Were Deposited
Name: National Institute of Bioscience and Human-Technology Agency of Industrial Science and Technology
Ministry of International Trade and Industry
Address: 1–3, Higashi 1-chome, Tsukuba-shi, Ibaraki-ken, Japan
Date of deposition thereof to the depository authority: Oct. 16, 1997
Depository Number Given by the Depository Author: FERM BP-6420
Name and Address of Depository Authority to Which Said Organisms of the Present Invention Were Deposited
Name: National Institute of Bioscience and Human-Technology
Agency of Industrial Science and Technology
Ministry of International Trade and Industry
Address: 1–3, Higashi 1-chome, Tsukuba-shi, Ibaraki-ken, Japan
Date of deposition thereof to the depository authority: Oct. 16, 1997
Depository Number Given by the Depository Author: FERM BP-6421

What is claimed is:

1. An isolated monoclonal antibody produced by a hybridoma selected from the group consisting of OI-4 having Accession No. FERM BP-6419, OI-19 having Accession No. FERM BP-6420, and OI-26 having Accession No. FERM BP-6421, and capable of recognizing osteoclastogenesis inhibitory factor protein.

2. The monoclonal antibody according to claim 1, wherein said monoclonal antibody recognizes different epitopes of said osteoclastogenesis inhibitory factor protein and has an affinity for an antigen of said osteoclastogenesis inhibitory factor protein that has a dissociation constant of less than about $2 \times 10^{-7}$ M.

3. The isolated monoclonal antibody of claim 1, wherein said monoclonal antibody is produced by hybridoma OI-4 having Accession No. FERM BP-6419.

4. The isolated monoclonal antibody of claim 1, wherein said monoclonal antibody is produced by hybridoma OI-19 having Accession No. FERM BP-6420.

5. The isolated monoclonal antibody of claim 1, wherein said monoclonal antibody is produced by hybridoma OI-26 having Accession No. FERM BP-6421.

6. Hybridoma selected from the group consisting of OI-4 having Accession No. FERM BP-6419, OI-19 having Accession No. FERM BP-6420, and OI-26 having Accession No. FERM BP-6421.

7. An assay kit for determination of osteoclastogenesis inhibitory factor protein concentration, comprising at least two monoclonal antibodies produced by a hybridoma, selected from the group consisting of OI-4 having Accession No. FERM BP-6419, OI-19 having Accession No. FERM BP-6420, and OI-26 having Accession No. FERM BP-6421, each of which recognize different epitopes of said osteoclastogenesis inhibitory factor protein.

8. The assay kit of claim 7, wherein at least one of said at least two monoclonal antibodies is produced by hybridoma OI-4 having Accession No. FERM BP-6419.

9. The assay kit of claim 7, wherein at least one of said at least two monoclonal antibodies is produced by hybridoma OI-19 having Accession No. FERM BP-6420.

10. The assay kit of claim 7, wherein at least one of said at least two monoclonal antibodies is produced by hybridoma OI-26 having Accession No. FERM BP-6421.

11. An assay kit for measuring osteoclastogenesis inhibitory factor protein concentration for diagnosing metabolic bone disease in a mammal, comprising at least one monoclonal antibody produced by a hybridoma selected from the group consisting of OI-4 having Accession No. FERM BP-6419, OI-19 having Accession No. FERM BP-6420, and OI-26 having Accession No. FERM BP-6421 each of which recognizes different epitopes of osteoclastogenesis inhibitory factor protein.

12. An assay kit for diagnosis of a metabolic disease using synovial fluid, comprising:
at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, each of which recognizes different epitopes of osteoclastogenesis inhibitory factor protein.

13. An assay kit for diagnosis of a metabolic bone disease using blood or serum, comprising:
at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, each of which recognizes different epitopes of osteoclastogenesis inhibitory factor protein.

14. A method of diagnosing metabolic bone disease in a mammal, said method comprising the steps of:
(a) contacting a test blood sample taken from said mammal with at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, and that binds specifically to an osteoclastogenesis inhibitory factor protein to produce an antibody-osteoclastogenesis inhibitory factor complex;
(b) determining the concentration of said antibody-osteoclastogenesis inhibitory factor complex in said test blood sample;
(c) comparing the concentration of said antibody-osteoclastogenesis inhibitory factor complex in said test blood sample to a standard curve to determine the concentration of osteoclastogenesis inhibitory factor protein; and,
(d) comparing the concentration of said osteoclastogenesis inhibitory factor protein in said test blood sample with a concentration of osteoclastogenesis inhibitory factor protein in a normal patient blood sample, wherein an elevated concentration of said osteoclastogenesis inhibitory factor protein in said test blood sample relative to said normal patient blood sample is indicative of metabolic bone disease in said mammal.

15. The method of claim 14, wherein said concentration of said osteoclastogenesis inhibitory factor protein in said test blood sample is elevated relative to said normal patient blood sample, as determined by an enzyme-linked immunoassay.

16. The method of claim 14, wherein said monoclonal antibody binds monomer type of osteoclastogenesis inhibitory factor protein or homodimer type of osteoclastogenesis inhibitory factor protein.

17. The method of claim 14, wherein said monoclonal antibody binds osteoclastogenesis inhibitory factor protein homodimer type.

18. The method of claim 14, wherein said monoclonal antibody binds to said osteoclastogenesis inhibitory factor protein with a dissociation constant of less than about $2 \times 10^{-7}$ M.

19. The method of claim 14, wherein said monoclonal antibody is labeled with a detectable label.

20. The method of claim 14, wherein said metabolic bone disease is osteoporosis.

21. The method of claim 14, wherein said metabolic bone disease is arthritis.

22. The method of claim 14, wherein said metabolic bone disease is rheumatoid arthritis.

23. The method of claim 14, wherein said monoclonal antibody is produced by hybridoma OI-4 having Accession No. FERM BP-6419.

24. The method of claim 14, wherein said monoclonal antibody is produced by hybridoma OI-19 having Accession No. FERM BP-6420.

25. The method of claim 14, wherein said monoclonal antibody is produced by hybridoma OI-26 having Accession No. FERM BP-6421.

26. A method of detecting metabolic bone disease in an individual, said method comprising the steps of:
   (a) contacting a test blood sample drawn from said individual with at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, or an antigen binding domain thereof, and that binds specifically to osteoclastogenesis inhibitory factor protein;
   (b) measuring in the test blood sample the quantity per unit volume of said osteoclastogenesis inhibitory factor protein, or a fragment thereof, bound by the antibody or the antigen binding domain thereof; and,
   (c) comparing the quantity per unit volume of said osteoclastogenesis inhibitory factor protein in said test blood sample, with a value of osteoclastogenesis inhibitory factor protein per unit volume from a patient without metabolic bone disease, wherein an altered quantity per unit volume of said osteoclastogenesis inhibitory factor protein in said test blood sample relative to the value of said osteoclastogenesis inhibitory factor protein from a patient without metabolic disease is indicative of the presence of metabolic bone disease in said individual.

27. The method of claim 26, wherein said monoclonal antibody is labeled with a detectable label.

28. The method of claim 26, wherein said metabolic bone disease is osteoporosis.

29. The method of claim 26, wherein said metabolic bone disease is arthritis.

30. The method of claim 26, wherein said metabolic bone disease is rheumatoid arthritis.

31. The method of claim 26, wherein said monoclonal antibody is produced by hybridoma OI-4 having Accession No. FERM BP-6419.

32. The method of claim 26, said monoclonal antibody is produced by hybridoma OI-19 having Accession No. FERM BP-6420.

33. The method of claim 26, wherein said monoclonal antibody is produced by hybridoma OI-26 having Accession No. FERM BP-6421.

34. A method of diagnosing the progression of metabolic bone disease in a patient, said method comprising the steps of:
   (a) contacting a blood sample taken from said patient with at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, and that binds specifically to an osteoclastogenesis inhibitory factor protein to produce an antibody-osteoclastogenesis inhibitory factor complex;
   (b) determining the concentration of said antibody-osteoclastogenesis inhibitory factor complex in said patient blood sample;
   (c) comparing the concentration of said antibody-osteoclastogenesis inhibitory factor complex to a standard curve to determine the concentration of osteoclastogenesis inhibitory factor protein; and,
   (d) comparing the concentration of said osteoclastogenesis inhibitory factor in said patient blood sample with a concentration of osteoclastogenesis inhibitory factor in a sample previously obtained from said patient, wherein an elevated concentration of said osteoclastogenesis inhibitory factor in said patient blood sample relative to said concentration in said blood sample previously obtained from said patient, is indicative of progression of metabolic bone disease.

35. The method of claim 34, wherein said monoclonal antibody is produced by hybridoma OI-4 having Accession No. FERM BP-6419.

36. The method of claim 34, wherein said monoclonal antibody is produced by hybridoma OI-19 having Accession No. FERM BP-6420.

37. The method of claim 34, wherein said monoclonal antibody is produced by hybridoma OI-26 having Accession No. FERM BP-6421.

38. A method of diagnosing metabolic bone disease in a mammal, said method comprising the steps of:
   measuring the concentration of osteoclastogenesis inhibitory factor protein in a test sample comprising synovial fluid isolated from said mammal;
   comparing the concentration of said osteoclastogenesis inhibitory factor protein in said test sample with a concentration of osteoclastogenesis inhibitory factor protein from a normal patient synovial fluid sample, wherein a decreased concentration of said osteoclastogenesis inhibitory factor protein in said test synovial fluid sample relative to the normal patient synovial fluid sample, is indicative of metabolic bone disease in said mammal.

39. The method of claim 38, wherein said metabolic bone disease is osteoporosis.

40. The method of claim 38, wherein said metabolic bone disease is rheumatoid arthritis.

41. The method of claim 38, wherein the step for measuring the concentration of osteoclastogenesis inhibitory factor protein in a test sample comprising synovial fluid further comprises the steps of:
   contacting the test sample with at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, and that binds specifically to an osteoclastogenesis inhibitory factor protein to produce an antibody-osteoclastogenesis inhibitory factor complex;
   determining the concentration of said antibody-osteoclastogenesis inhibitory factor complex in said test sample; and,
   comparing the concentration of said antibody-osteoclastogenesis inhibitory factor complex in said test sample to a standard curve to determine the concentration of osteoclastogenesis inhibitory factor protein.

42. The method of claim 38, wherein said step for measuring the concentration of osteoclastogenesis inhibitory factor protein in a test sample comprising synovial fluid further comprises the steps of:
  contacting the test sample with at least one monoclonal antibody that binds specifically to an osteoclastogenesis inhibitory factor protein to produce an antibody-osteoclastogenesis inhibitory factor complex;
  determining the concentration of said antibody-osteoclastogenesis inhibitory factor complex in said test sample; and,
  comparing the concentration of said antibody-osteoclastogenesis inhibitory factor complex in said test sample to a standard protein curve to determine the concentration of osteoclastogenesis inhibitory factor protein.

43. A method of diagnosing metabolic bone disease in a mammal, said method comprising the steps of:
  (a) contacting a test synovial fluid sample taken from said mammal with a monoclonal antibody produced by a hybridoma selected from the group consisting of OI-4 having Accession No. FERM BP-6419, OI-19 having Accession No. FERM BP-6420, and OI-26 having Accession No. FERM BP-6421, and that binds specifically to an osteoclastogenesis inhibitory factor protein to produce an antibody-osteoclastogenesis inhibitory factor complex;
  (b) determining the concentration of said antibody-osteoclastogenesis inhibitory factor complex in said test synovial fluid sample;
  (c) comparing the concentration of said antibody-osteoclastogenesis inhibitory factor complex in said test synovial fluid sample to a standard protein curve to determine the concentration of osteoclastogenesis inhibitory factor protein; and,
  (d) comparing the concentration of said osteoclastogenesis inhibitory factor protein in said test synovial fluid sample with a concentration of osteoclastogenesis inhibitory factor protein in a normal patient sample, wherein a decreased concentration of said osteocloastogenesis inhibitory factor protein in said test synovial fluid sample relative to said normal patient sample is indicative of metabolic bone disease in said mammal.

44. The method of claim 43, wherein said concentration of said osteoclastogenesis inhibitory factor in said test synovial fluid sample is lower relative to said normal patient synovial fluid sample, as determined by enzyme-linked immunoassay.

45. The method of claim 43, wherein said monoclonal antibody binds monomer type of osteoclastogenesis inhibitory factor protein or homodimer type of osteoclastogenesis inhibitory factor protein.

46. The method of claim 43, wherein said monoclonal antibody binds osteoclastogenesis inhibitory factor protein homodimer type.

47. The method of claim 43, wherein said monoclonal antibody binds to osteoclastogenesis inhibitory factor protein with a dissociation constant of less than about $2 \times 10^{-7}$ M.

48. The method of claim 43, wherein said monoclonal antibody is labeled with a detectable label.

49. The method of claim 43, wherein said metabolic bone disease is osteoporosis.

50. The method of claim 43, wherein said metabolic bone disease is arthritis.

51. The method of claim 43, wherein said metabolic bone disease is rheumatoid arthritis.

52. The method of claim 43, wherein said monoclonal antibody is produced by hybridoma OI-4 having Accession No. FERM BP-6419.

53. The method of claim 43, wherein said monoclonal antibody is produced by hybridoma OI-19 having Accession No. FERM BP-6420.

54. The method of claim 43, wherein said monoclonal antibody is produced by hybridoma OI-26 having Accession No. FERM BP-6421.

55. The method of claim 43, wherein at least two monoclonal antibodies produced by a hybridoma selected from the group consisting of OI-4 having Accession No. FERM BP-6419, OI-19 having Accession No. FERM BP-6420, and OI-26 having Accession No. FERM BP-6421, each of which binds to a different epitope of an osteoclastogenesis inhibitory factor protein, are contacted with said test synovial fluid sample.

56. The assay for detecting metabolic bone disease of claim 55, wherein at least one of said at least two monoclonal antibodies is produced by hybridoma OI-4 having Accession No. FERM BP-6419.

57. The assay for detecting metabolic bone disease of claim 55, wherein at least one of said at least two monoclonal antibodies is produced by hybridoma OI-19 having Accession No. FERM BP-6420.

58. The assay for detecting metabolic bone disease of claim 55, wherein at least one of said at least two monoclonal antibodies is produced by hybridoma OI-26 having Accession No. FERM BP-6421.

59. A method of detecting metabolic bone disease in an individual, said method comprising the steps of:
  (a) contacting a test synovial fluid sample drawn from said individual with at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, or an antigen binding domain thereof, and that binds specifically to osteoclastogenesis inhibitory factor protein;
  (b) measuring in the test synovial fluid sample the quantity per unit volume of osteoclastogenesis inhibitory factor protein, bound by the antibody or said antigen binding domain thereof; and,
  (c) comparing the quantity per unit volume of said osteoclastogenesis inhibitory factor protein in said test synovial fluid sample, with a value of osteoclastogenesis inhibitory factor protein per unit volume from a patient without metabolic bone disease, wherein a lowered quantity per unit volume of said osteoclastogenesis inhibitory factor protein, in said test synovial fluid sample relative to the value of said osteoclastogenesis inhibitory factor protein from said patient without metabolic bone disease, is indicative of the presence of metabolic bone disease in said individual.

60. The method of claim 59, wherein said monoclonal antibody is labeled with a detectable label.

61. The method of claim 59, wherein said metabolic bone disease is osteoporosis.

62. The method of claim 59, wherein said metabolic bone disease is arthritis.

63. The method of claim 59, wherein said metabolic bone disease is rheumatoid arthritis.

64. The method of claim 59, wherein said monoclonal antibody is producing by hybridoma OI-4 having Accession No. FERM BP-6419.

65. The method of claim 59, wherein said monoclonal antibody is produced by hybridoma OI-19 having Accession No. FERM BP-6420.

66. The method of claim 59, wherein said monoclonal antibody is produced by hybridoma OI-26 having Accession No. FERM BP-6421.

67. A method of diagnosing the progression of metabolic bone disease in a patient, said method comprising the steps of:
(a) contacting a synovial fluid sample taken from said patient with at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, and that binds specifically to an osteoclastogenesis inhibitory factor protein to produce an antibody-osteoclastogenesis inhibitory factor complex;
(b) determining the concentration of said antibody-osteoclastogenesis inhibitory factor complex in said patient synovial fluid sample;
(c) comparing the concentration of said antibody-osteoclastogenesis inhibitory factor complex to a standard curve to determine the concentration of osteoclastogenesis inhibitory factor protein; and,
(d) comparing the concentration of said osteoclastogenesis inhibitory factor in said patient synovial fluid sample with a concentration of osteoclastogenesis inhibitory factor in a synovial fluid sample previously obtained from said patient, wherein a decreased concentration of said osteoclastogenesis inhibitory factor in said patient synovial fluid sample relative to said concentration in said synovial fluid sample previously obtained from said patient, is indicative of progression of metabolic bone disease.

68. The method of claim 67, wherein said monoclonal antibody is produced by hybridoma OI-4 having Accession No. FERM BP-6419.

69. The method of claim 67, wherein said monoclonal antibody is produced by hybridoma OI-19 having Accession No. FERM BP-6420.

70. The method of claim 67, wherein said monoclonal antibody is produced by hybridoma OI-26 having Accession No. FERM BP-6421.

71. A method of diagnosing metabolic bone disease in a mammal, said method comprising the steps of:
measuring a concentration of osteoclastogenesis inhibitory factor protein in a test blood sample isolated from said mammal; and,
comparing said concentration of osteoclastogenesis inhibitory factor protein in a test blood sample with a concentration of osteoclastogenesis inhibitory factor protein in a normal patient blood sample, wherein an increase in said concentration of osteoclastogenesis inhibitory factor protein in a test blood sample relative to the normal patient blood sample, is indicative of metabolic bone disease in said mammal,
wherein the step of measuring said concentration of osteoclastogenesis inhibitor factor protein in a test blood sample further comprises the steps of:
contacting said test blood sample isolated from said mammal with at least one monoclonal antibody produced by a hybridoma selected from the group consisting of OI-4 having Accession No. FERM BP-6419, OI-19 having Accession No. FERM BP-6420, and OI-26 having Accession No. FERM BP-6421, and that binds specifically to said osteoclastogenesis inhibitory factor protein to produce an antibody-osteoclastogenesis inhibitory factor complex;
determining the concentration of said antibody-osteoclastogenesis inhibitory factor complex in said test blood sample; and,
comparing the concentration of said antibody-osteoclastogenesis inhibitory factor complex in said test blood sample to a standard curve to determine the concentration of osteoclastogenesis inhibitory factor protein.

72. The method of claim 71, herein said test blood sample is contacted with a plurality of said monoclonal antibodies.

* * * * *